US012318237B2

(12) United States Patent
Damany et al.

(10) Patent No.: US 12,318,237 B2
(45) Date of Patent: Jun. 3, 2025

(54) REMOTE AND AUTOMATED INTENSIVE CARE UNIT (71) Applicant: CARESTREAM HEALTH, INC., Rochester, NY (US)

(72) Inventors: Dharmendu Damany, Woodinville, WA (US); Xiaohui Wang, Pittsford, NY (US); William J. Sehnert, Fairport, NY (US); John Yorkston, Arlington, VA (US); David H. Foos, Webster, NY (US); Eliot L. Siegel, Severna Park, MD (US)

(73) Assignee: Carestream Health, Inc., Rochester, NY (US)

( * ) Notice: Subject to any disclaimer, the term of this patent is extended or adjusted under 35 U.S.C. 154(b) by 256 days.

(21) Appl. No.: 18/246,337

(22) PCT Filed: Oct. 20, 2021

(86) PCT No.: PCT/US2021/055720
§ 371 (c)(1),
(2) Date: Mar. 23, 2023

(87) PCT Pub. No.: WO2022/087047
PCT Pub. Date: Apr. 28, 2022

(65) Prior Publication Data
US 2023/0371912 A1 Nov. 23, 2023

Related U.S. Application Data (60) Provisional application No. 63/094,924, filed on Oct. 22, 2020.

(51) Int. Cl.
A61B 6/00 (2024.01)
A61B 6/04 (2006.01)
(Continued)

(52) U.S. Cl.
CPC .......... *A61B 6/4452* (2013.01); *A61B 6/0407* (2013.01); *A61B 6/08* (2013.01);
(Continued)

(58) Field of Classification Search
CPC .......... A61B 6/40; A61B 6/4021; A61B 6/02; A61B 6/0407; A61B 6/00; A61B 6/0405;
(Continued)

(56) References Cited

U.S. PATENT DOCUMENTS 9,820,703 B2  11/2017  Wojcik et al.
10,709,004 B2  7/2020  Blasio
(Continued)

FOREIGN PATENT DOCUMENTS

DE  37 32 194 A1  4/1988
EP  2 389 865 A1  11/2011

OTHER PUBLICATIONS

International Search Report mailed on Jan. 25, 2022 for International Application No. PCT/US2021/055720, 3 pages.

*Primary Examiner* — Don K Wong (57) ABSTRACT

A radiographic imaging system may be deployed in an ICU unit of a medical facility that may benefit from isolating patients and health care providers. The radiography system provides a plurality of patient beds each having a digital radiographic detector positioned therein. An x-ray source is operable to be selectively positioned relative to each of the patient beds using a remote control system. The remote control system also controls firing of the x-ray source.

14 Claims, 6 Drawing Sheets

(51) Int. Cl.
  *A61B 6/08* (2006.01)
  *A61B 6/40* (2024.01)
  *A61B 6/42* (2024.01)
  *A61B 90/00* (2016.01)

(52) U.S. Cl.
  CPC .......... *A61B 6/4007* (2013.01); *A61B 6/4266* (2013.01); *A61B 6/4405* (2013.01); *A61B 6/4417* (2013.01); *A61B 6/4464* (2013.01); *A61B 6/548* (2013.01); *A61B 6/56* (2013.01); *A61B 2090/3937* (2016.02)

(58) Field of Classification Search
  CPC ....... A61B 6/42; A61B 6/4266; A61B 6/4283; A61B 6/46; A61B 6/467; A61B 6/547; A61B 6/548; A61B 2560/0487; G16H 30/00
  See application file for complete search history.

(56) References Cited

U.S. PATENT DOCUMENTS

| | | |
|---|---|---|
| 2005/0031087 A1 | 2/2005 | Maschke |
| 2015/0124940 A1* | 5/2015 | Kim .................. A61B 6/4283 378/189 |
| 2019/0076106 A1 | 3/2019 | Tkaczyk et al. |
| 2020/0000426 A1 | 1/2020 | Simon et al. |

\* cited by examiner

REMOTE AND AUTOMATED INTENSIVE CARE UNIT

CROSS REFERENCE TO RELATED APPLICATIONS

This application claims the benefit of and is a U.S. National Phase filing of PCT Application PCT/US2021/055720 filed Oct. 20, 2021 entitled "REMOTE AND AUTOMATED INTENSIVE CARE UNIT", in the name of Damany et al., which claims benefit of U.S. Patent Application Ser. No. 63/094,924, filed Oct. 22, 2020, in the name of Damany et al., and entitled REMOTE-AUTOMATED INTENSIVE CARE UNIT.

BACKGROUND OF THE INVENTION

The subject matter disclosed herein relates to remotely controlled and automated digital x-ray imaging systems and methods.

Infection control has emerged as being among the most critically important factors in healthcare delivery as a result of the global propagation of Covid 19. One consequence of the pandemic is that it has precipitated and accelerated the innovation process in a multitude of healthcare product arenas, including in areas such as personal protective equipment, ventilators, assays for Covid 19 testing, antimicrobials, among many others. In this regard there is great interest in building better infection control into the medical imaging process. In particular, in the context of portable x-ray imaging of patients in intensive care units, in emergency departments, and other medical care facilities. One approach for x-ray imaging that represents a shift in the imaging process does not require mobile x-ray units. The present invention makes use of an in-room imaging system for purposes of automation and remote control, thereby allowing patients afflicted with infectious disease to remain in isolation from staff that would normally perform the imaging at the patient bedside.

New facilities construction might be required in some instances, wherein patients who are afflicted with infectious disease are placed in isolation, either in a bay that is designated specifically for patients who are sick with the same particular disease (i.e., a Covid 19 ward), and the caregiving staff (nurses, physicians, therapists, etc.) are able to monitor and provide care remotely, e.g., from behind a wall with windows, as a means to minimize patient contact, and thereby also minimize the need for use of PPE. In such a scenario, vital signs monitoring, voice and visual communication mechanisms, and imaging would all need to be performed remotely and, preferably to the extent that technology and logistics would permit, be performed by automated means.

The discussion above is merely provided for general background information and is not intended to be used as an aid in determining the scope of the claimed subject matter.

BRIEF DESCRIPTION OF THE INVENTION

A radiographic imaging system may be deployed in an ICU unit of a medical facility that may benefit from isolating patients and health care providers. The radiography system provides a plurality of patient beds each having a digital radiographic (DR) detector positioned therein. An x-ray source is operable to be selectively positioned relative to each of the patient beds using a remote control system. The remote control system also controls firing of the x-ray source. An advantage that may be realized in the practice of some disclosed embodiments of the radiographic imaging system is isolation of health care providers from communicable pathogens shed by patients being radiographically imaged.

In one embodiment, a radiography system is installed in a plurality of patient beds wherein each bed includes a DR detector positioned therein. An x-ray source is configured to be selectively moved and positioned relative to each of the patient beds via a remote control system and is operable to be fired by the remote control system to capture radiographic images of patients while maintaining isolation of health care personnel away from the patients.

In one embodiment, a DR detector may be placed in every bed designated to hold a patient, an overhead tube crane type of mechanism having a collimated x-ray source, and motion control, either remote or automated, to position the x-ray source relative to the patient and a DR detector for x-ray image capture. Various aspects of the detector may be modified to achieve an advantageous solution. Preferably, a large form factor DR detector may be used (perhaps 17×17 inch or greater, e.g., 17×51 inch) to allow tolerance for source to detector positioning and/or misalignments. Fiducial markers on the bed, bed frame, or patient in preselected locations may be used to aid in the positioning of the x-ray tube (source) relative to patient and detector. An automatic exposure control (AEC) mechanism disposed in the bed may be used to control exposure times. In one embodiment, the DR detector may be tethered in the bed, so that it is always powered on, connected to facility digital communication network, and ready to capture exposure images without need for a battery. The DR detector may be selected for high frame rate to support advanced applications such as serial radiography, dual energy, and digital tomosynthesis. In one embodiment, the DR detector could be made inexpensively, such as by using GOS with artificial intelligence noise suppression vs. CsI, and without wireless capability. The housing could be simplified because the DR detector would not need to be manufactured robustly such as for preventing liquid ingress, breakage from drops, and other shocks.

The summary descriptions above are not meant to describe individual separate embodiments whose elements are not interchangeable. In fact, many of the elements described as related to a particular embodiment can be used together with, and possibly interchanged with, elements of other described embodiments. Many changes and modifications may be made within the scope of the present invention without departing from the spirit thereof, and the invention includes all such modifications.

This brief description of the invention is intended only to provide a brief overview of subject matter disclosed herein according to one or more illustrative embodiments, and does not serve as a guide to interpreting the claims or to define or limit the scope of the invention, which is defined only by the appended claims. This brief description is provided to introduce an illustrative selection of concepts in a simplified form that are further described below in the detailed description. This brief description is not intended to identify key features or essential features of the claimed subject matter, nor is it intended to be used as an aid in determining the scope of the claimed subject matter. The claimed subject matter is not limited to implementations that solve any or all disadvantages noted in the background.

BRIEF DESCRIPTION OF THE DRAWINGS

So that the manner in which the features of the invention can be understood, a detailed description of the invention may be had by reference to certain embodiments, some of which are illustrated in the accompanying drawings. It is to be noted, however, that the drawings illustrate only certain embodiments of this invention and are therefore not to be considered limiting of its scope, for the scope of the invention encompasses other equally effective embodiments. The drawings below are intended to be drawn neither to any precise scale with respect to relative size, angular relationship, relative position, or timing relationship, nor to any combinational relationship with respect to interchangeability, substitution, or representation of a required implementation, emphasis generally being placed upon illustrating the features of certain embodiments of the invention. In the drawings, like numerals are used to indicate like parts throughout the various views. Thus, for further understanding of the invention, reference can be made to the following detailed description, read in connection with the drawings in which.

DETAILED DESCRIPTION OF THE INVENTION

This application claims priority to U.S. Patent Application Ser. No. 63/094,924, filed Oct. 22, 2020, in the name of Foos et al., and entitled REMOTE-AUTOMATED INTENSIVE CARE UNIT, which is hereby incorporated by reference herein in its entirety.

This application is related in certain respects to U.S. Pat. No. 10,709,004, having Ser. No. 15/967,963, filed May 1, 2018, in the name of Anthony J. BLASIO, and entitled OVERHEAD TUBE CRANE GUIDE, which is hereby incorporated by reference herein in its entirety; and to U.S. Pat. No. 9,820,703, having Ser. No. 14/942,081, filed Nov. 16, 2015, in the name of Wojcik, et al., and entitled TILED DIGITAL RADIOGRAPHY DETECTORS FOR LONG-LENGTH IMAGING, which is hereby incorporated by reference herein with respect to FIGS. 1-4 therein and their description.

Figure 1A:
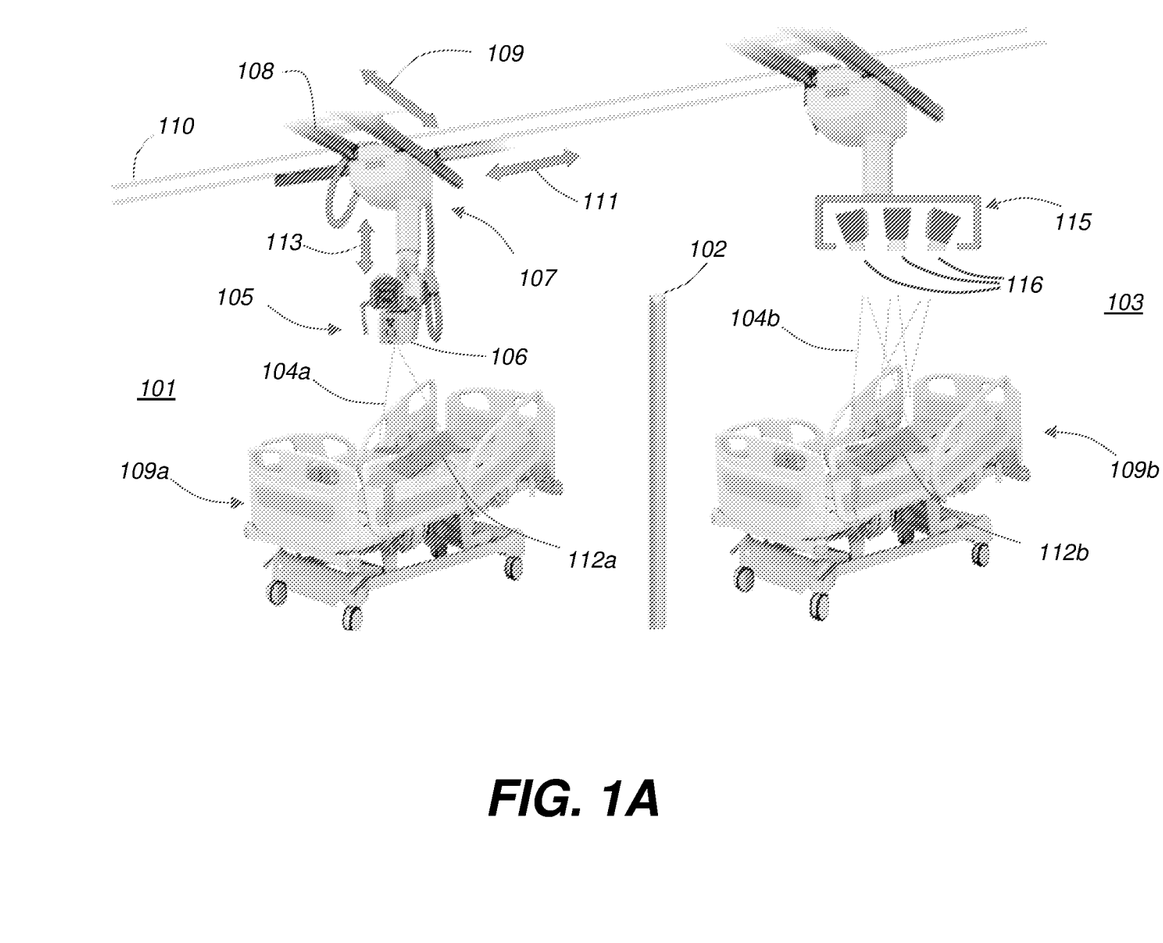
FIGS. 1A and 1B are perspective views of exemplary radiographic imaging systems useable with ICU beds.

FIG. 1A illustrates exemplary radiographic imaging systems that may be deployed in medical imaging facilities such as in adjacent ICU patient rooms 101 and 103. The adjacent ICU rooms 101, 103 may be separated by a divider 102, such as a fixed solid structural wall, a movable solid wall, a curtain, or a drape, for example. As shown in FIG. 1A, a movable tube head 105 includes an x-ray source, and has a collimator 106 attached thereto, which tube head 105 may be mounted on an overhead tube crane 107. The collimator 106 may include an electronically controlled collimator 106 having four individually movable blades for controlling a size of a rectangular aperture. The overhead tube crane 107 may be attached to a first track 108 to allow remote controlled movement of the tube crane 107 along directions 109 thereon. The overhead tube crane 107 may also be attached to a second track 110 to allow remote controlled movement of the tube crane 107 along directions 111 thereon. Typically, the movement directions 109, 111 may be configured to be perpendicular to each other and both parallel to a ceiling of a room containing the radiographic imaging system. The overhead tube crane 107 may also be configured to be telescopically extended and retracted vertically along directions 113. The tracks 108, 110 may be attached to, and extend along, a ceiling bridging ICU patient rooms 101, 103. Thus, the tube crane 107 may be used to controllably move the tube head 105 from one ICU room to another ICU room, such as above and over the divider 102, within a medical facility having a plurality of ICU rooms. The tube crane 107 includes an electric motor for controllably driving the tube crane 107 along a selected track 108, 110. Movement of the tube crane 107 along tracks 108, 110, allows accurate positioning of the tube head 105 in relation to either of patient beds 109a. 109b. In particular, movement of the tube crane 107 along tracks 108, 110, allows controlled positioning of the tube head 105 in relation to either of DR detectors 112a and 112b positioned in patient beds 109a, 109b, respectively. After controllably positioning the tube head 105 in relation to DR detector 112a, for example, the x-ray source therewithin may be remotely and controllably fired to emit x-ray beam 104a to expose DR detector 112a. As described in detail herein, such positioning of the tube head 105 and x-ray exposures may be performed remotely without requiring personnel to be present in the ICU rooms 101, 103.

In a separate embodiment, a tube head 115 having multiple x-ray sources 116, such as carbon nanotube or other cold cathode sources, may be similarly mounted on, and operated by, an overhead tube crane 107 as described herein above. Movement of the tube head 115 using tube crane 107 along tracks 108, 110, allows controlled positioning of the x-ray sources 116 in relation to either of DR detectors 112a and 112b positioned in patient beds 109a, 109b, respectively. After controllably positioning the x-ray sources 116 in relation to DR detector 112b, for example, the x-ray sources 116 may be remotely and controllably fired to emit one or more separate x-ray beams 104b to expose DR detector 112b. As described in detail herein, such positioning of the x-ray sources 116 and x-ray exposures may be performed remotely without requiring personnel to be present in the ICU rooms 101, 103. Although two different tube heads 105, 115, are shown together in FIG. 1A for illustrative purposes, it is to be understood that only one remote controlled movable tube head 105 or 115 is required by the present invention for movement along tracks 108, 110.

Figure 1B:
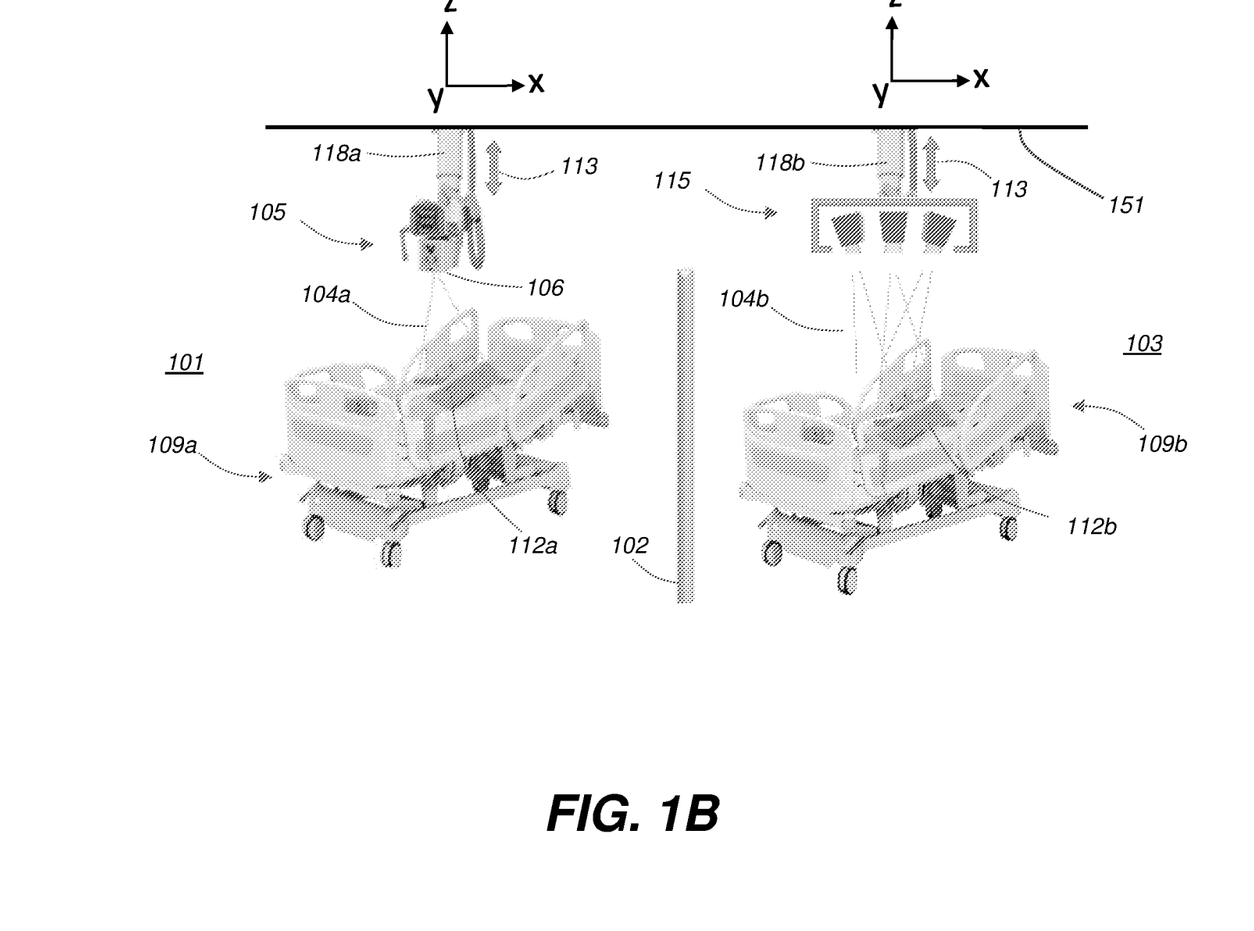

FIG. 1B illustrates an exemplary radiographic imaging system that may be deployed in medical imaging facilities such as ICU patient rooms 101 and 103, described herein above. The ICU rooms 101, 103 may be separated by a divider 102, such as a fixed solid structural wall, a movable solid wall, a curtain, or a drape, for example. As shown in FIG. 1B, a tube head 105 having an x-ray source, and a collimator 106 attached thereto, may be fixably mounted on support 118A attached to a ceiling 151 of ICU room 101. Alternatively, the tube head 105 containing an x-ray source and collimator 106 may be mounted on a wall of ICU room 101. Similarly, a tube head 115 including multiple x-ray sources, such as carbon nanotube or other cold cathode sources, may be fixably mounted on a support 118b attached to the ceiling 151 of a ICU room 103. Alternatively, the tube head 115 containing multiple x-ray sources may be mounted on a wall of ICU room 103. The tube heads 105, 115, may be rotatably attached to supports 118a, 118b, respectively, such that the tube heads 105, 115, may be rotated about any of orthogonal axes x, y, or in order to align the x-ray sources with DR detectors 112a, 112b, positioned in the patient beds 109a, 109b, respectively. The tube heads 105, 115, may also be extended and retracted vertically along directions 113. The supports 118a, 118b, may each include a motor that is remotely controllable to rotate and extend/retract the tube heads 105, 115. Rotational and vertical movement of the tube heads 105, 115, allows accurate positioning of the x-ray sources therewithin in relation to the DR detectors 112a, 112b, respectively. After controllably positioning the tube head 105 in relation to DR detector 112a, for example, the x-ray source therewithin may be remotely and controllably fired to emit an x-ray beam 104a to expose DR detector 112a, as described herein above. After controllably positioning the tube head 115 in relation to DR detector 112b, for example, the x-ray sources 116 therewithin may be remotely and controllably fired to emit one or more an x-ray beams 104b to expose DR detector 112b, as described herein above. As further described in detail herein, such positioning of individual tube heads 105, 115, one in each patient room 101, 103, and their x-ray exposures may be performed remotely without requiring personnel to be present in the ICU rooms 101, 103.

Figure 2:
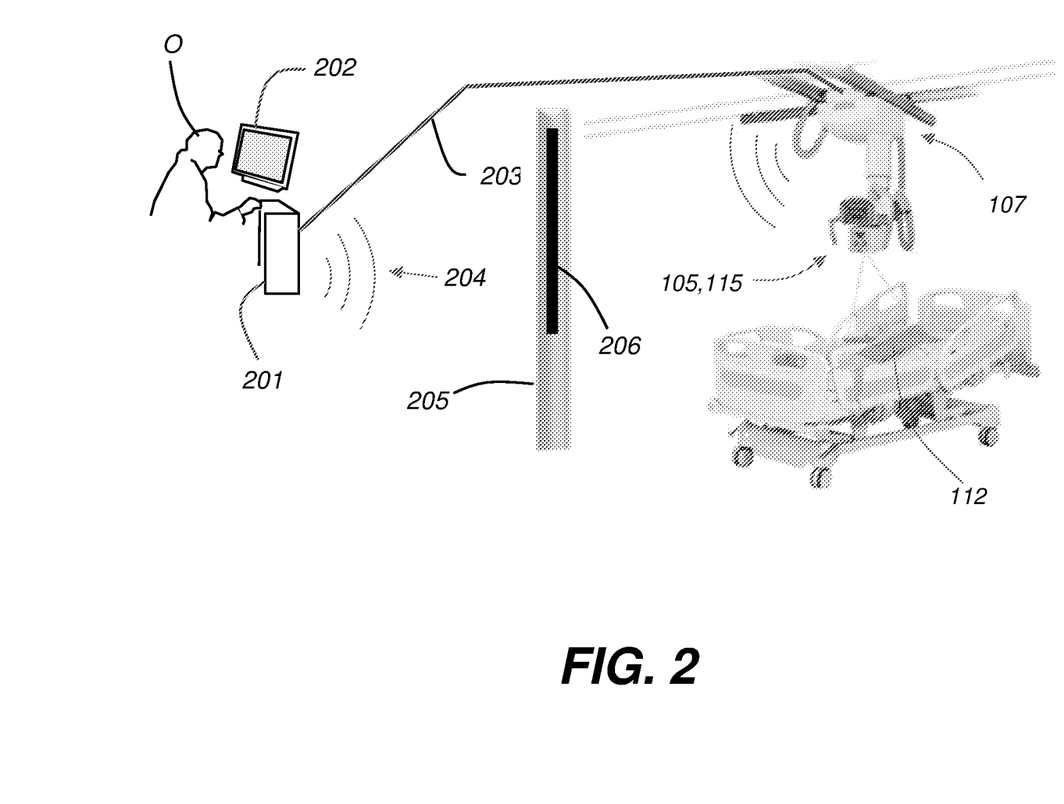
FIG. 2 is an exemplary control system for operating the radiographic imaging systems.

The schematic diagram of FIG. 2 illustrates an exemplary embodiment of a radiographic imaging system as described herein. The embodiment described with respect to FIG. 2 may be used with any of the previous embodiments described herein with respect to FIGS. 1A-1B. A user control console 201 may include a processing system for remotely controlling operation of the radiographic imaging systems described herein. The processing system may include a wired coupling 203 or a wireless transmission capability 204 for communicating with and controlling movement and operation of the tube crane 107 as well as the tube head 105, 115, and the x-ray sources therein, such as a power level and/or firing sequence of the x-ray sources, and timing of exposures to be captured by DR detector 112. The control console 201 includes connected I/O devices such as a keyboard/mouse and a digital operator display 202 for operator O use. In addition, the control console 201 may communicate by wire or wirelessly with DR detector 112, if the DR detector 112 is so equipped, such as to transmit captured radiographic images to the control console 201, and for synchronizing an image capture sequence of the DR detector 112 with firing of the x-ray source(s) in tube head 105, 115. The control console 201 may then transmit captured radiographic images to other network connected devices over a wired or wireless channel, such as to hand held tablets and cell phones. The control console 201 may be electronically connected to a medical facility communication network where the radiographic imaging system is installed.

The control console 201 may be separated from the patient rooms 101, 103, by one or more walls 205, to provide an environment for operator O that is isolated from the patient rooms 101, 103. The control console 201 may be used by operator O to obtain radiographic images of patients in patient rooms 101, 103, without requiring operator O to have a direct line of sight of the patient P (FIG. 3) or patient rooms 101, 103. The control console 201 may be located in a control room of a medical facility on a different floor from the patient rooms 101, 103, or even in a different building of the medical facility. If the medical facility network, which includes the control console 201, is connected to the internet then the control console 201 may be configured to be operable over the internet from hundreds of miles away, thereby allowing the radiography system disclosed herein to be used remotely by operators over large distances. In a separate embodiment, the control system 201 may be configured and located at a particular site so that operator O may have a line of sight view of the patient P and the patient bed 109, such as by providing a window 206 in isolation wall 205 through which the operator O can directly view the patient P.

Figure 3:
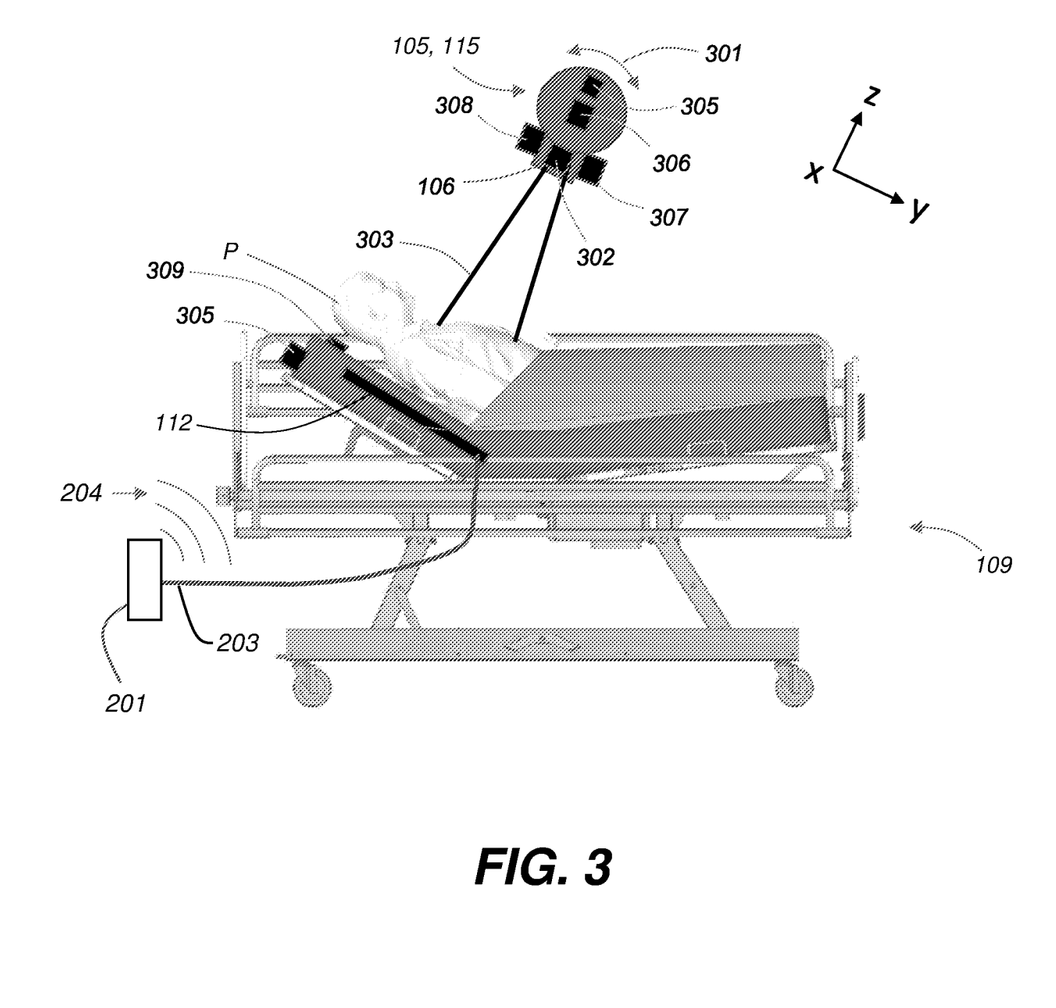
FIG. 3 is a schematic illustration showing operation of the exemplary radiographic imaging systems.

FIG. 3 illustrates a side view of the radiographic imaging system of the present invention. A patient P may be lying on an ICU room bed 109 having a DR detector 112 positioned therewithin as described with reference to FIGS. 1A-B herein. A tube head 105, 115 having an x-ray source 306 is controllably rotated in directions 301 about axis x, for example, and about axes z and y, as necessary, by an operator P using control console 201 as described herein. A light projector 302 attached, for example, inside the collimator 106 may be used to project a light beam 303 for illuminating a radiation field, or exposure area, on the patient P in order to verify alignment of the x-ray source 306 with an area of the patient P to be radiographically imaged. As is known to those skilled in the art, a light source 302 may be configured to transmit a light beam 303 through the aperture of collimator 106 that coincides with an optical path of an x-ray beam to be emitted by x-ray source 306 through the same aperture. The DR detector 112 may be fixed in position within the patient bed 109. The DR detector 112 may be connected to the control console 201 by wire 203, which wire 203 may include data communication lines as well as power supply lines for operating the detector 112, or the DR detector 112 may communicate wirelessly 204 with the control console 201 if so equipped. The tube head 105, 115, and the DR detector 112 may each include a corresponding accelerometer 305 which transmits spatial orientation data to the control console 201 to aid in verifying alignment of the tube head 105, 115, and the DR detector 112. The accelerometer 305 associated with detector 112 may be positioned in or on the patient bed 109 in a known position and distance relative to the detector 112. The term accelerometer may be used interchangeably herein with terms such as inclinometer, inertial sensor and tilt sensor. A range finder 307 attached to the tube head 105, 115, using ultrasound signals or lasers aimed at the patient bed 109, for example, may be implemented to precisely measure source to detector distance (SID). A video camera 308 may be mounted on the tube head 105, 115, to aid in alignment of the tube head 105, 115, by transmitting a video signal over wire 203, or wirelessly, to the operator display 202. Fiducial markers 309 may be positioned on the patient P or on the patient bed 109, which fiducial markers 309 may be used by an operator to assist in aligning the tube head 105, 115, with respect to DR detector 112. The fiducial markers 309 may be positioned in locations having known distances and spatial orientations relative to the detector 112.

Figure 4:
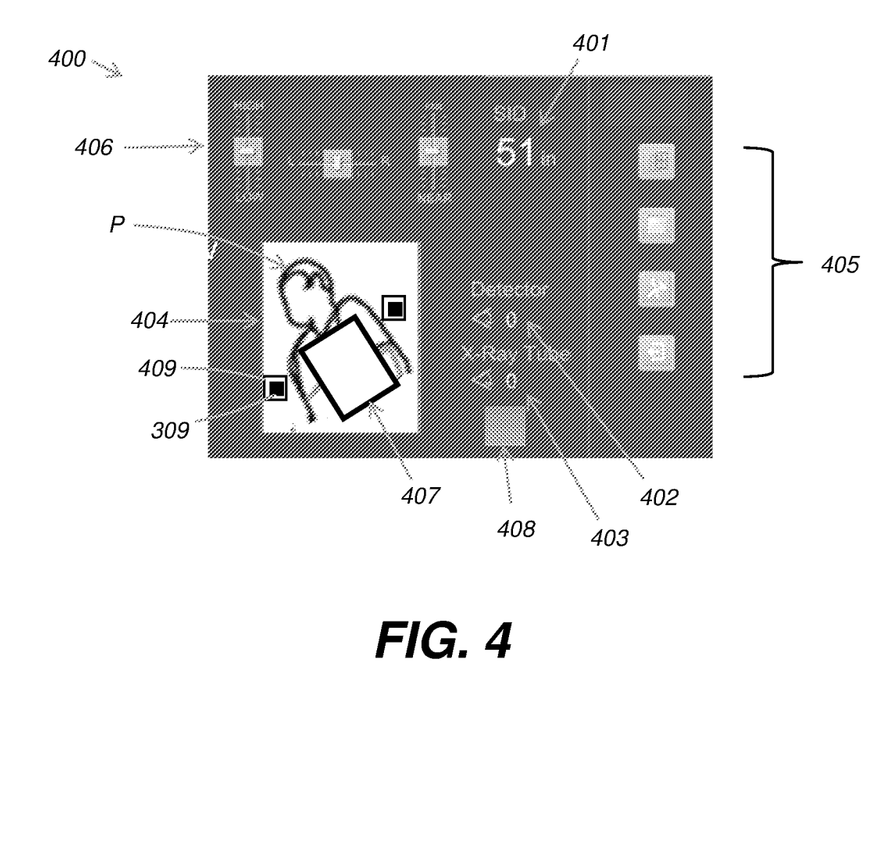
FIG. 4 illustrates an example display and control screen for remote operation of the exemplary radiographic imaging system.

FIG. 4 illustrates an exemplary configuration of a graphical user interface (GUI) 400 to display control data and to provide operator controls, which may be presented on digital operator display 202 as described herein with reference to FIG. 2. The GUI 400 may be used to display a calculated SID 401 measured by range finder 307, a calculated relative detector tilt angle 402, a calculated relative tube head tilt angle 403, a video camera display 404 transmitted by video camera 308 to display to an operator a video of the position of the patient P and the illuminated radiation area 407 as illuminated by light source 302, and controls 406 for adjusting a spatial position of the tube head 105, 115, along tracks 108, 110, or vertically along directions 113, and angularly along axes x, y and z (FIG. 1B). GUI controls 405 may be selected by the operator to selectively display a different set of functions 406 to control other parameters of the radiographic imaging system as described herein, and to display other numerical data fields. The exemplary GUI 400 may be a part of a touch screen implementation for operator control of the radiographic imaging system and it may also serve as a status display wherein control devices, such as knobs, keyboards, mouse, buttons, etc., of the radiographic imaging system may be positioned on other components thereof. An operator may use remote positioning controls 406 while viewing the live video of patient P on camera display 404 in order to properly position the radiation field on patient P as illuminated by light source 302. The operator can also use remote positioning controls 406 to move and align the tube head 105, 115, into a parallel orientation with detector 112 using the detector tilt angle 402 and tube head tilt angle 403 displays so that the emitted x-rays 104 may be as close to a perpendicular (90°) orientation to the detector 112 as possible. After a proper alignment is achieved, the x-ray source (s) in the tube head 105, 115, may be controllably fired, using source firing control 408, to capture radiographic images of the patient P in the DR detector 112. A precisely and selectively positioned fiducial marker 309 may be captured by video camera 308 and shown in video display 404 for use by an operator to properly align the tube head 105, 115, with the DR detector 112. For example, operator display screen cursors 409, provided in the GUI 400, may be used by an operator while adjusting a position of the tube head 105, 115, to establish proper alignment with the fiducial markers 309. Such a fiducial alignment indicates to the operator that a proper alignment has been achieved as between the tube head 105, 115, and the detector 112. Thus, an operator may use the fiducial markers 309 and display cursors 409, or the illuminated radiation area 407 appearing in the video camera display 404 for remote alignment purposes.

Figure 5:
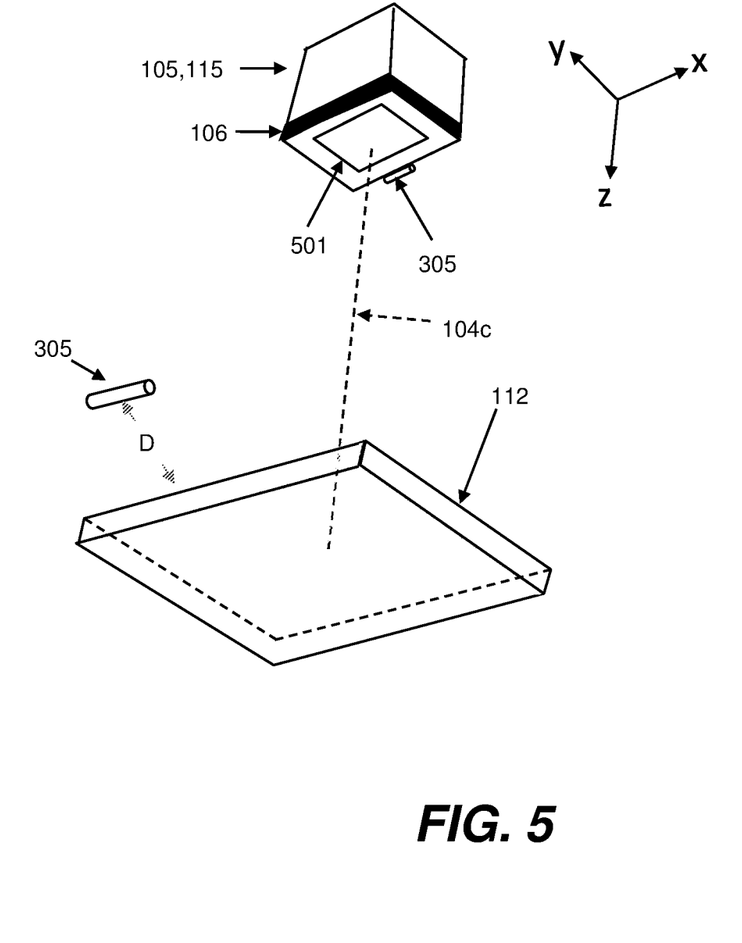
FIG. 5 illustrates an alignment system that may be combined with the exemplary radiographic imaging systems.

FIG. 5 is a schematic display of a tube head 105, 115, having an electronic collimator 106 with a rectangular aperture 501 and a three-dimensional inclinometer/accelerometer 305 to illustrate use of accelerometers 305 for alignment of the radiographic imaging system. Another inclinometer 305 is positioned in the patient bed 109 (FIG. 3) in a known spatial relationship and distance D from the detector 112. The inclinometers 305 may generate and transmit data to the control console 201, as described herein, identifying their spatial orientation with respect to three dimensional coordinates x, y and z. Such three-dimensional coordinate data may be used by the processing system of control console 201 to calculate an angular value identifying a displacement of the tube head 105, 115, and DR detector 112 away from a parallel orientation therebetween, whereby a parallel orientation may be represented by an angular displacement value of 0°. In particular, an angular displacement of 0° may also be interpreted to indicate that a substantially central ray 104c of an x-ray beam collimated by collimator 106 impacts the DR detector 112 at an angle close to about 90°, i.e., the central ray 104c is perpendicular to a surface of the DR detector 112. The angular displacement value may be interpreted as generally pertaining to planes occupied by a plane of the planar DR detector 112 and to the plane occupied by the rectangular aperture 501 of the collimator 106.

The DR detector 112 may include a two dimensional array of addressable photosensitive cells (pixels). The DR detector 112 may be positioned within a patient bed, as described herein, to receive a collimated x-ray beam 104 passing through a patient P lying on a bed 109 during radiographic imaging. As shown in FIGS. 1A-B, the radiographic imaging system may use an x-ray source that emits collimated x-rays, e.g. an x-ray beam 104, selectively aimed at and passing through a preselected region of the patient P. The DR detector 112 is positioned underneath patient P in a perpendicular relation, as much as possible, to a substantially central ray 104c of the x-ray beam 104. The DR detector 112 may communicate with the central control console 201 over a wireless transmitter or over a wired connection to transmit radiographic image data thereto. The control console 201 may include a processing system having electronic memory and may also be used to control the x-ray sources, an aperture size and shape of an electronic collimator 106, a projection angle of the x-ray beam 104 relative to the tube head 105, 115, by manipulating the electronic collimator aperture, the tube head 105, 115, electric current magnitude to tube head 105, 115, and thus the fluence and energy level of x-rays in x-ray beam 104. The control console 201 may transmit images and other data to the connected digital display 202 for display thereon. In one embodiment, the accelerometers 305 may be configured to transmit their three-dimensional tilt coordinates to the processing console 201. The console 201 may be configured to calculate a respective planar positions of the DR detector 112 and the collimator 106 to determine an angular displacement of the DR detector 112 and the tube head 105, 115, relative to a parallel orientation thereof. The angular displacement so determined may be displayed on the digital operator display 202, which displacement may include a calculated displacement having a zero value which indicates that the tube head 105, 115, and the detector 112 are disposed parallel to each other. The angular displacement may include a calculated displacement having an example 30° value which indicates that the tube head 105, 115, and the DR detector 112 are displaced from a parallel orientation by 30°.

Collimator blades contained in the electronic collimator 401 control a shape and size of an aperture 501 of the collimator and, thereby, a radiation area on the DR detector 112, which radiation area receives x-rays of the x-ray beam 104 generated and emitted by an x-ray source 306. The collimator blades may be configured as a pair of parallel blades forming a rectangular aperture, which blades may be individually adjustable under programmed motor control. Control instructions for adjusting the electronic collimator aperture 501 may be transmitted from the console 201, which may also receive positioning feedback data from the collimator 106 indicating precise height and width dimensions of the electronic collimator aperture 501, which precise height and width dimensions may then be numerically displayed on the digital display 202.

ALTERNATIVE EMBODIMENTS

In the embodiment of FIG. 1B, small and inexpensive monoblock x-ray sources may be used with each patient bed or ICU room. The monoblock sources could be ceiling mounted or mounted on the wall adjacent to the bed. In one embodiment, an array of stationary sources (tube head 115) might be used for digital tomosynthesis capture at high speed. The video camera 308 could also be used for respiratory gating to synchronize exposures of the patient P. Artificial intelligence (AI) software may be used for automated positioning before exposure such as by storing encoder data used in previous exposures. AI may also be used for automated exposure technique determination, for automated quality control of captured x-ray images, such as a reject/accept analysis, for gridless capture and image processing, for display processing optimization, noise cancellation, and companion view generation, for sparse sampling approaches to minimize capture time for SR, DT, and DE, for detection of acute degradation in patient respiratory status, and to generate alerts for primary care givers. The AI software may be used in a parallel data path for AI tomosynthesis capture, with AI findings layered on standard general radiation images (with synthesized optimal projection) for ICU physicians. The AI software may also be used for prognostic outlook prediction based on digital vital signs, drug dosages, history, more than two dimensional (& longitudinal) imagery, and for automated tube/line tip localization and monitoring catheter position.

In one embodiment, an integrated remote PC, such as in console 201, may be used for motion control, patient communication, and patient monitoring. In one embodiment, a ceiling mounted visible light (and IR) camera can be used to monitor the patient 24 hours a day. Imagery from the camera can be used to automatically determine if an x-ray needs to be taken, e.g., by sensing respiratory distress or some other patient condition that is worsening. An infrared camera can be used to detect changes in patient temperature, such as coming from exhaled breath. Such a camera could be a stereo camera to monitor chest movement more precisely in 3D. Incorporated infection control features can include various uses of anti-microbials on surfaces. A microphone may be included that listens to patient 24 hours a day, coupled with AI automated interpretation to sense audio that might be coupled with patient distress. An air quality monitoring system could also be added to provide indications to hospital staff when it may be more or less safe to enter the patient room to provide care.

Advantages that may be realized in the practice of some disclosed embodiments of the automated intensive care unit include clinical, workflow, and financial benefits. A fully remote and semi-automated image acquisition procedure provides infection control, improved image quality and consistency versus mobile DR imaging, and ICU operation with fewer staff to reduce hospital operational costs. Standard and advanced x-ray capture modes are more easily enabled as compared to a portable x-ray machine. Higher dimensional (greater than 2D) imagery leads to improved patient care for patients that are either too sick to be moved, or for patients having respiratory infectious disease that can't be moved due to concerns over unnecessarily exposing hospital staff and equipment. Tomosynthesis, dynamic, and dual energy improves information content and thereby enabling AI interpretation and processing to be highly robust. Improved automated change analysis and associated alerts for staff in the event a decline in patient condition is detected.

As will be appreciated by one skilled in the art, aspects of the present invention may be embodied as a system, method, or computer program product. Accordingly, aspects of the present invention may take the form of an entirely hardware embodiment, an entirely software embodiment (including firmware, resident software, micro-code, etc.), or an embodiment combining software and hardware aspects that may all generally be referred to herein as a "service." "circuit," "circuitry." "module." and/or "system." Furthermore, aspects of the present invention may take the form of a computer program product embodied in one or more computer readable medium(s) having computer readable program code embodied thereon.

Any combination of one or more computer readable medium(s) may be utilized. The computer readable medium may be a computer readable signal medium or a computer readable storage medium. A computer readable storage medium may be, for example, but not limited to, an electronic, magnetic, optical, electromagnetic, infrared, or semiconductor system, apparatus, or device, or any suitable combination of the foregoing. More specific examples (a non-exhaustive list) of the computer readable storage medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a computer readable storage medium may be any tangible medium that can contain, or store a program for use by or in connection with an instruction execution system, apparatus, or device.

Program code and/or executable instructions embodied on a computer readable medium may be transmitted using any appropriate medium, including but not limited to wireless, wireline, optical fiber cable, RF, etc., or any suitable combination of the foregoing.

Computer program code for carrying out operations for aspects of the present invention may be written in any combination of one or more programming languages, including an object oriented programming language such as Java, Smalltalk, C++ or the like and conventional procedural programming languages, such as the "C" programming language or similar programming languages. The program code may execute entirely on the user's computer (device), partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

Aspects of the present invention are described herein with reference to flowchart illustrations and/or block diagrams of methods, apparatus (systems) and computer program products according to embodiments of the invention. It will be understood that each block of the flowchart illustrations and/or block diagrams, and combinations of blocks in the flowchart illustrations and/or block diagrams, can be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or block diagram block or blocks.

The computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or block diagram block or blocks.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims.

The invention claimed is:

1. A radiography system comprising:
a plurality of patient beds each comprising a DR detector positioned therein;
a remote control system; and
an x-ray source configured to be selectively positioned relative to each of the patient beds via the remote control system and configured to be fired via the remote control system.

2. The system of claim 1, further comprising:
a plurality of x-ray sources fixed in position relative to each other in a tube head and configured to be fired by the remote control system in a predetermined sequence.

3. The system of claim 1, further comprising a video camera attached adjacent to the x-ray source and aimed at one of the patient beds, and a digital display to display video captured by the video camera.

4. The system of claim 3, further comprising at least one fiducial marker placed on or proximate to each of the patient beds, each of the at least one fiducial marker positioned at a known position and distance relative to a corresponding DR detector, the fiducial markers each configured to be visible on the digital display when the corresponding patient bed is displayed thereon.

5. The system of claim 1, wherein the DR detectors are each connected by wire to a source of electric power.

6. The system of claim 5, wherein the DR detectors are each connected by a wire to a computer system for digitally communicating therewith.

7. The system of claim 1, further comprising a range finder attached adjacent to the x-ray source to determine a distance between the x-ray source and the DR detector, the range finder configured to transmit the determined source to detector distance to the remote control system.

8. The system of claim 1, wherein the remote control system comprises a video display screen showing a video image of at least one of the patient beds, and wherein the remote control system is located at a site without a direct line of sight view of any of the patient beds.

9. A method of operating a radiographic imaging system, the method comprising the steps of:
using a remote control system, remotely viewing on a video screen a video image of a first patient in a first patient bed, the first patient bed comprising a first DR detector;
moving an x-ray source into a first alignment with respect to the first DR detector using the remote control system;
firing the x-ray source using the remote control system to capture a radiographic image of the first patient in the first DR detector;
using the remote control system, remotely viewing on the video screen a video image of a second patient in a second patient bed while moving the x-ray source away from the first patient bed toward the second patient bed, the second patient bed comprising a second DR detector;
moving the x-ray source into a second alignment with respect to the second DR detector using the remote control system; and
firing the x-ray source using the remote control system to capture a radiographic image of the second patient in the second DR detector.

10. The method of claim 9, further comprising transmitting the radiographic image of the first patient from the first DR detector to the remote control system and transmitting the radiographic image of the second patient from the second DR detector to the remote control system.

11. The method of claim 9, wherein the first patient bed is located in a first patient room, the second patient bed is located in a second patient room, the first patient room is isolated from the second patient room by a wall, and wherein the first and second patient rooms are isolated from the remote control system.

12. The method of claim 9, wherein the step of moving the x-ray source into the first alignment comprises viewing on the video screen an illuminated radiation area projected onto the first patient.

13. The method of claim 9, wherein the step of moving the x-ray source into the first alignment comprises aligning on the video screen a fiducial marker positioned on the first patient bed with a screen cursor provided on the video screen.

14. The method of claim 9, further comprising displaying on the video screen orientation data in alphanumerical form, the orientation data for indicating an amount of deviation from a preferred alignment as between the x-ray source and the first DR detector.

* * * * *